(12) United States Patent
Vincent-Prestigiacomo (10) Patent No.: US 7,322,982 B2
(45) Date of Patent: *Jan. 29, 2008

(54) POSITION-ADJUSTMENT DEVICE WITH APPLICABILITY FOR SURGICAL INSTRUMENTATION

(75) Inventor: Philippe Vincent-Prestigiacomo, Lacanau Océan (FR)

(73) Assignee: Stryker Spine (FR)

( * ) Notice: Subject to any disclaimer, the term of this patent is extended or adjusted under 35 U.S.C. 154(b) by 489 days.

This patent is subject to a terminal disclaimer.

(21) Appl. No.: 10/867,043

(22) Filed: Jun. 14, 2004

(65) Prior Publication Data

US 2004/0243127 A1    Dec. 2, 2004

Related U.S. Application Data

(60) Provisional application No. 10/054,840, filed on Jan. 23, 2002, now Pat. No. 6,783,528.

(30) Foreign Application Priority Data

Jan. 23, 2001    (FR) ................... 01 00873

(51) Int. Cl.
*A61B 17/56* (2006.01)
*A61F 2/30* (2006.01)

(52) U.S. Cl. ........................................ 606/61
(58) Field of Classification Search ............ 606/53, 606/60, 61, 86, 103, 151; 24/115 M, 136 R
See application file for complete search history.

(56) References Cited

U.S. PATENT DOCUMENTS

| 731,635 A | 6/1903 | Vandegrift |
|---|---|---|
| 1,258,580 A | 3/1918 | Lassiter |
| 3,758,922 A | 9/1973 | Field |
| 3,868,748 A | 3/1975 | Kelly |
| 3,952,377 A | 4/1976 | Morell |
| 4,653,481 A | 3/1987 | Howland et al. |
| 4,881,302 A | 11/1989 | Lee |
| 5,074,864 A | 12/1991 | Cozad et al. |
| 5,122,131 A | 6/1992 | Tsou |
| 5,281,222 A | 1/1994 | Allard et al. |
| 5,330,473 A | 7/1994 | Howland |
| 5,507,746 A | 4/1996 | Lin |
| 5,615,965 A | 4/1997 | Saurat et al. |
| 5,653,708 A | 8/1997 | Howland |

(Continued)

FOREIGN PATENT DOCUMENTS

DE    199 60 718 A1    12/2000

(Continued)

OTHER PUBLICATIONS

P.L. Pavy, Service De La Propriete Industrielle, Brevet D'Invention Imprime et Edite Le, May 5, 1961. PRIX: 20 FR.

*Primary Examiner*—Anuradha Ramana
(74) *Attorney, Agent, or Firm*—Lerner, David, Littenberg, Krumholz & Mentlik, LLP (57) ABSTRACT

A position-adjustment device having particular applicability for surgical instrumentation. The system comprises a body connected to an elongate member in such an arrangement as to have interchangeable locked and unlocked states. In the unlocked state, the body is free to move along the elongate member, and in the locked state the body is prevented from moving along the elongate member.

30 Claims, 5 Drawing Sheets

U.S. PATENT DOCUMENTS

| | | |
|---|---|---|
| 5,681,351 A | 10/1997 | Jamiolkowski et al. |
| 5,682,796 A | 11/1997 | Malone |
| 5,685,199 A * | 11/1997 | Malone ................. 74/502.4 |
| 5,776,134 A | 7/1998 | Howland |
| 5,888,197 A | 3/1999 | Mulac et al. |
| 6,115,890 A | 9/2000 | Silagy |
| 6,783,528 B2 * | 8/2004 | Vincent-Prestigiacomo .. 606/61 |

FOREIGN PATENT DOCUMENTS

| | | |
|---|---|---|
| EP | 1 023 873 A2 | 8/2000 |
| WO | WO-98 29046 A1 | 7/1998 |

* cited by examiner

POSITION-ADJUSTMENT DEVICE WITH APPLICABILITY FOR SURGICAL INSTRUMENTATION

CROSS-REFERENCE TO RELATED APPLICATIONS

This is a continuation application of U.S. Ser. No. 10/054,840, filed Jan. 23, 2002, now U.S. Pat. No. 6,783,528, which claims priority of French Application No. 0100873 filed on Jan. 23, 2001.

BACKGROUND OF THE INVENTION

The invention relates to a position adjustment device having particular applicability to surgical instrumentation.

In the event of traumas, simple or multiple fractures of one or more vertebrae in the spine can give rise to various configurations that require corrective movements to be applied in order to return the spine to its original shape, in particular concerning the curvature involved in lordosis and kyphosis. Special instruments are used for this purpose that make such restoration possible in cooperation with osteosynthesis systems that are known from elsewhere. Document DE G-91-12 466.2 describes such instrumentation including an adjustment system which comprises a threaded rod having two oppositely-handed threads situated on either side of drive means. Each of the threads engages in a tapped bore of a body connected to an element of the instrumentation. Operating such a system is lengthy because of the pitch of the threads and also because of the fact that during handling, surgical gloves come into contact with the threads which have sharp edges that are liable to catch and tear the gloves, thus requiring additional precautions to be taken. This lengthens the time required to perform an operation which increases the likelihood of harm to the patient.

SUMMARY OF THE INVENTION

An object of the invention is to provide an adjustment device for instrumentation for surgery of the spine, which can be put into place precisely and quickly.

To do this, according to the invention, there is provided a position-adjustment device, with particular applicability for surgical instrumentation, in particular for surgery of the spine. The device is used with an elongate member, which, as known to those of ordinary skill in the art of surgical instrumentation, is suitable for being connected to a first element of a surgical instrument. The device further comprises a body suitable for being fastened to the elongate member and for being connected to a second element of the surgical instrument, as well as a connection for connecting the elongate member to the body. The device is arranged to have an unlocked state in which the connection allows the elongate member to slide relative to the body and a locked state in which the connection prevents the elongate member from sliding relative to the body.

Thus, the unlocked state enables adjustment of position to be performed simply, precisely, and quickly, while the locked state enables the selected position to be locked quickly. As a result, such a device can be operated simply, precisely, and quickly.

Advantageously, the connection is arranged to prevent the elongate member from sliding relative to the body by a wedging effect.

Advantageously, the connection comprises at least one elastically deformable element.

Advantageously, the deformable element is suitable for implementing a wedging effect.

Advantageously, the device is arranged in such a manner that in the locked state, sliding is locked in a single direction.

Advantageously, the deformable element presents a bearing surface, and the elongate member presents a contact face suitable for coming into contact with the bearing surface in the locked state.

Thus, the longitudinal member entrains the deformable element towards the locked position because of the contact between the contact face and the bearing surface and without any intervention by the operator on the deformable element. The operator does not act on the deformable element, so the operator's hands do not come into contact with sharp edges. As a result there is no risk of damaging or tearing gloves during the operation.

Advantageously, the contact face is smooth, locking being obtained by friction.

Advantageously, the contact face is knurled.

Advantageously, the bearing surface includes knurling.

Advantageously, the contact face presents recesses, in particular grooves.

Advantageously, the bearing surface has a projection suitable for being received in the recesses.

Advantageously, the deformable element is split over all or part of its length.

Advantageously, the deformable element has deformable tongues at one end.

Advantageously, the deformable element has an end for implementing unlocking.

Advantageously, the deformable element is conical in shape.

Advantageously, the end for implementing unlocking includes a bearing rim.

Advantageously, the connection includes a second elastically deformable element.

Advantageously, the second deformable element is suitable for preventing sliding in the other direction of displacement.

Advantageously, the second deformable element is a mirror image of the first deformable element.

Advantageously, the body can be dismantled into at least two portions.

Advantageously, the body includes a connection for interconnecting the two portions, in particular, a ring.

BRIEF DESCRIPTION OF THE DRAWINGS

Other characteristics and advantages of the present invention appear from the following description of an embodiment. In the accompanying drawings:

FIG. 3b is a section view along line 3b through the deformable element of FIG. 3a;

DETAILED DESCRIPTION

Figure 1:
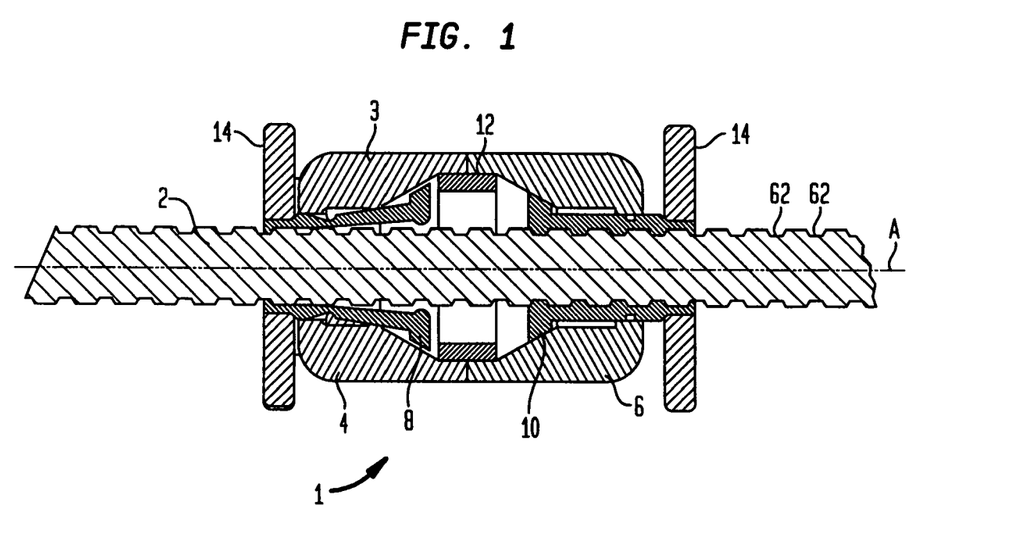
FIG. 1 is a section view of an embodiment of the invention shown in full.

An embodiment of the invention is described with reference to the figures. In FIG. 1, the position-adjustment device 1 comprises a hollow body 3 suitable for slidably receiving an elongate member, or rod 2, of circular section, together with a pair of elastically deformable elements 8 and 10 each having a circular plate 14 fixed to one end thereof.

The hollow body 3 comprises two half-shells 4 and 6 interconnected by a ring 12. The half-shell 6 is a mirror image of the half-shell 4 about a plane perpendicular to the axis of revolution A of the body 3. Only one half-shell is therefore described in detail.

Figure 2:
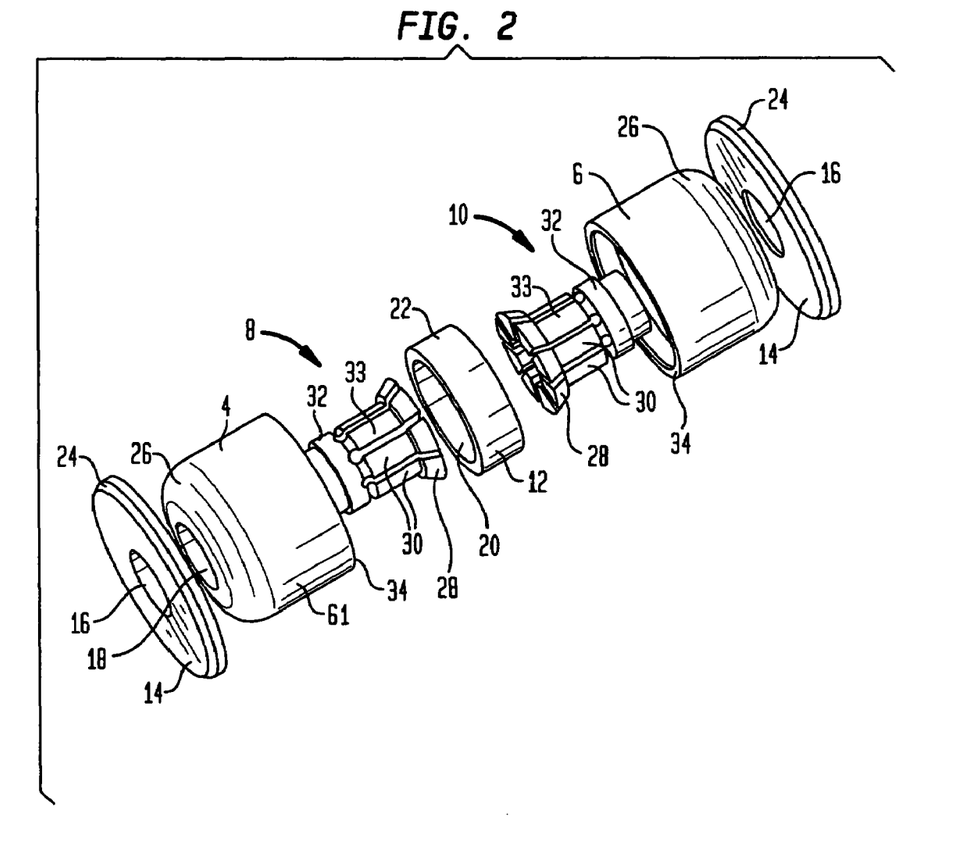
FIG. 2 is an exploded perspective view of the FIG. 1 embodiment without the elongate member.
Figure 4A:
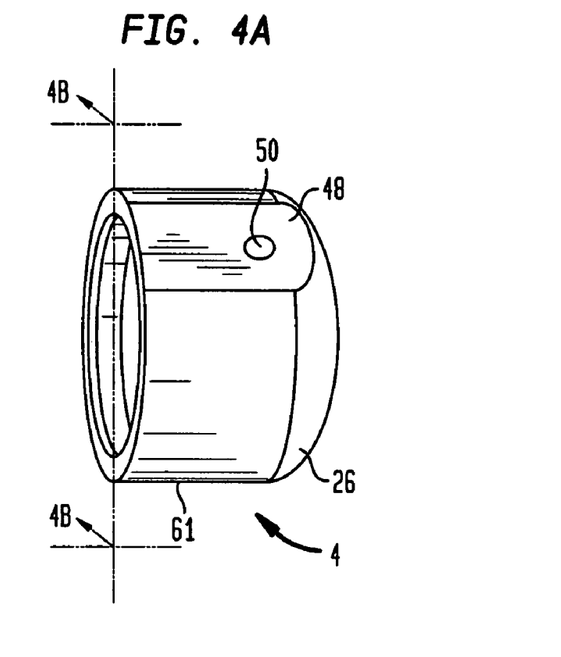
FIG. 4a is a perspective view of a fraction of the body of the FIG. 1 embodiment of the invention.
Figure 4B:
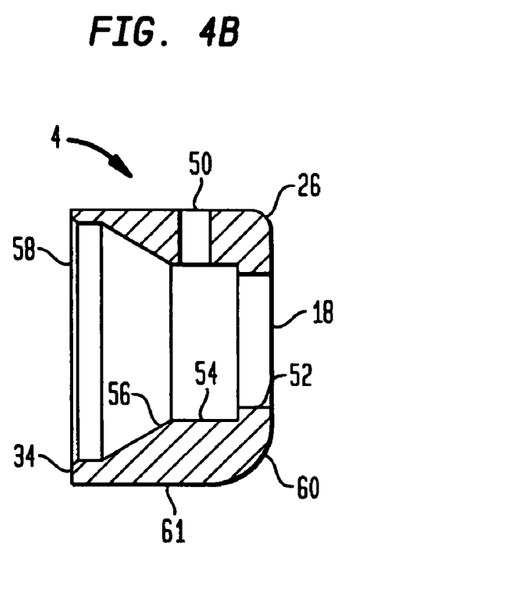
FIG. 4b is a section view along line 4b of the FIG. 4a body portion.

With reference to FIGS. 2, 4a, and 4b, the half-shell 4 has a through orifice 18 extending along its axis of revolution A. The half-shell 4 has an outside surface 61 and two axial end surfaces 34 and 60. The end surface 60 joins the outside surface 61 via a surface 26 of rounded shape. A portion of the outside surface 61 is replaced by a flat 48 parallel to the axis of revolution A. Perpendicular to this flat 48, a radial through tapped orifice 50 opens out to the inside of the orifice 18. The orifice 18 is made up of a plurality of portions: a cylindrical first portion of circular section defined by a surface 52 presents a first diameter; then a second cylindrical portion of circular section defined by a surface 54 presents a second diameter greater than the diameter of the first portion. The tapped orifice 50 opens out into this portion. A third portion is in the form of a frustoconical surface 56 which extends the orifice 18 causing it to expand from the diameter of the second portion to the diameter of a fourth portion, itself defined by a forth cylindrical portion having a cylindrical surface 58 of circular section. It is explained below that the surface 56 forms a bearing surface.

The ring 12 for interconnecting the two symmetrical half-shells 4 and 6 has a cylindrical outside face 22 whose diameter is substantially equivalent to the diameter of the fourth portion of each of the half-shells. The ring 12 also presents a cylindrical inside surface 20. The length of the ring 12 is equivalent to twice the width of the fourth portion of each of the half-shells 4 and 6.

The body 3 is formed as follows: the ring 12 is inserted in the fourth portion of the orifice 18 of the first half-shell. Because of its double width, once the ring 12 has been put into place in the first half-shell, it projects from the face 34 of the half-shell. Thereafter, the second half-shell is engaged on the ring 12 until its face 34 comes to bear against the face 34 of the first half-shell. The body 3 is thus completely formed. The outside diameter of the ring 12 and the inside diameter of the fourth portion in each of the half-shells are selected in such a manner that the ring is inserted as a force-fit so as to be capable of holding the body 3 together while it is in use during surgery, while nevertheless remaining separable by a theatre nurse to enable the device to be cleaned completely between two operations. In order to make assembly more secure, a link element (not shown) can optionally be used to join the two half-shells 4 and 6 together. The link element may be fixed to the half-shells by means of threaded members (not shown) suitable for engaging the tapping in the orifices 50 of each of the half-shells 4 and 6, the link element being suitable for bearing against the flats 48.

Figure 3A:
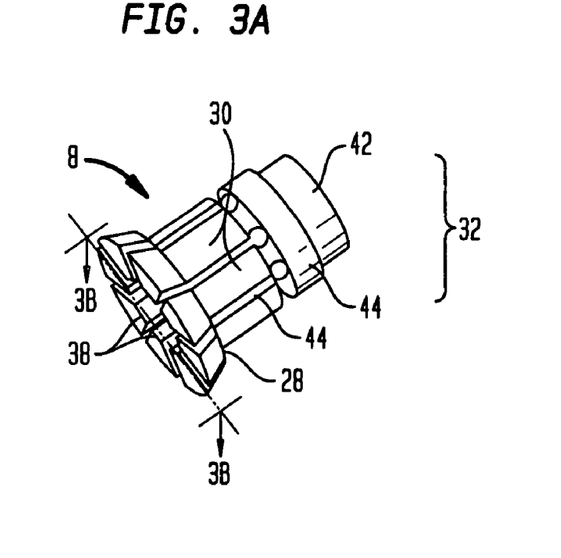
FIG. 3a is a perspective view of the deformable element of the FIG. 1 embodiment of the invention.
Figure 3B:
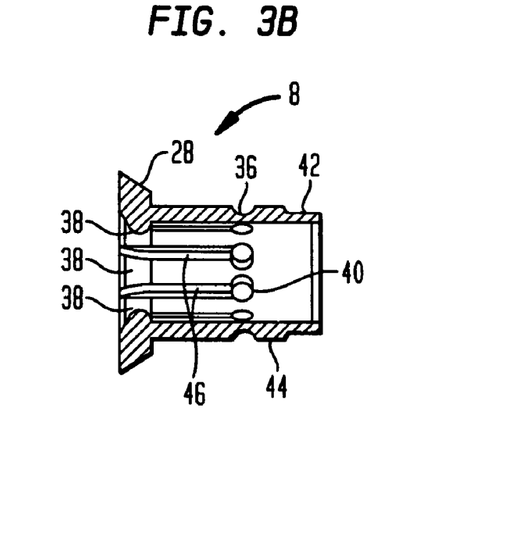

With reference to FIGS. 2, 3a, and 3b, there follows a description of the deformable elements 8 and 10. Element 10 is a mirror image of element 8 about a plane perpendicular to the axis of revolution A of the elements. Only one of the two elements is therefore described. Elastically deformable element 8 comprises two main portions 32 and 33. The general shape of the deformable element 8 is that of a tube. The portion 32 presents a first cylindrical surface 42 with a first diameter and a second surface 44 with a second diameter slightly greater than the diameter of the surface 42. The portion 32 is separated from the portion 33 of deformable element 8 by a concave groove 36 forming a complete circle around deformable element 8 and occupying a plane perpendicular to its axis. Portion 33 of deformable element 8 is made up of a plurality of tongues 30 that are uniformly distributed over the entire circumference of element 8. In this case, there are eight tongues 30. Each tongue 30 is separated from the next tongue by a slot 46 extending from the groove 36 to the free axial end of portion 33 of element 8. In the groove 36, each slot 46 becomes a circular through orifice 40. At the free end of portion 33 of deformable element 8, each tongue 30 is terminated by a projection extending radially outwards relative to element 8, and presenting a surface 28 that is conical in shape. Still at its free end, opposite surface 28, each tongue has a convex projection that is preferably of circular section extending radially towards the inside of deformable element 8. As explained below, portion 33 is the portion of element 8 which deforms in use. This deformation is due to each tongue being suitable for deforming essentially in the vicinity of the groove 36.

The diameter of surface 44 is substantially equivalent to the diameter of the first portion of orifice 18 defined by surface 52. The diameter of surface 42 is substantially equivalent to the diameter of orifice 16 present in the plates 14 that are described briefly, below.

The plates 14 constitute rings, each presenting a through orifice 16 and a rounded outer rim 24. The plates 14 are suitable for being mounted on portion 32 of each of the deformable elements 8, 10, so as to cover its surface 42. With reference to FIG. 1, the elongate member 2, suitable for being received inside body 3, is a circular section rod on the axis of revolution A, and presents a plurality of circumferential grooves 62 that are uniformly distributed along its entire length. These grooves 62 are of circular section.

The following is a description of how the position-adjustment device 1 is assembled. The first deformable element 8 is inserted in the half-shell 4, for example, in such a manner that the surface 44 occupies the first portion of the orifice 18, in contact with surface 52. Thereafter, a first plate 14 is mounted as a force-fit on portion 32 of first deformable element 8 in such a manner that the orifice 16 of the plate 14 receives the surface 42 of the deformable element. Then the ring 12 is inserted as a force-fit into the fourth portion of the orifice 18 of the half-shell in such a manner that surface 22 is in contact with surface 58. Thereafter, the second deformable element 10 is inserted in the second half-shell 6 in the same manner as deformable element 8 was inserted in the first half-shell 4, and then still in the same manner, the second plate 14 is put into place on portion 32 of deformable element 10. Finally, the second half-shell 6 is inserted on the ring 12 so as to close the body 3 as a whole. It should be observed that in each of the half-shells, each of the deformable elements is retained at one end by the presence of plate 14 on its portion 32 and at its other end by the presence of the projections having surfaces 28 at the ends of tongues 30 since each of the surfaces 28 is suitable for coming into contact with the surface 56 of the orifice 18. Secondly, when plate 14 comes into contact with the rear face 60 of a half-shell, the surface 28 of each of the tongues 30 is spaced apart from the surface 56 of the half-shell. Conversely, when each of the surfaces 28 of each of the tongues 30 is in contact with the surface 56 of the half-shell, then the plate 14 is no longer in contact with the surface 60 of the half-shell. Finally, in use, the elongate member 2 is then inserted into the assembly.

Figure 5:
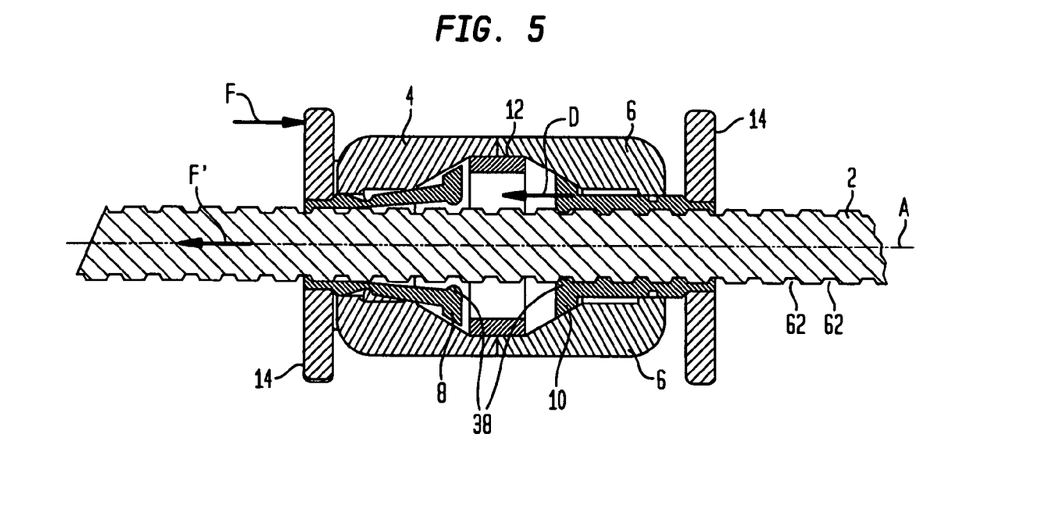
FIGS. 5 and 6 are section views through the FIG. 1 embodiment while it is in operation.
Figure 6:
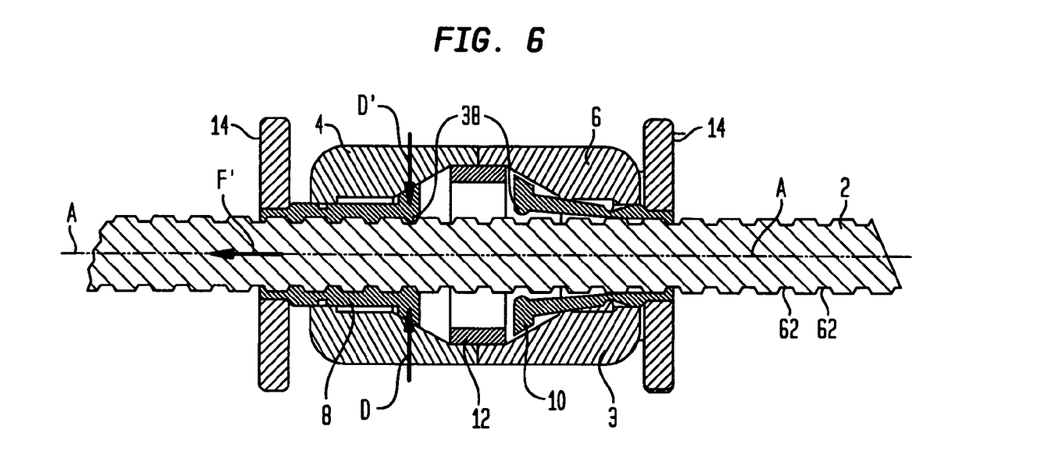
Figure 7:
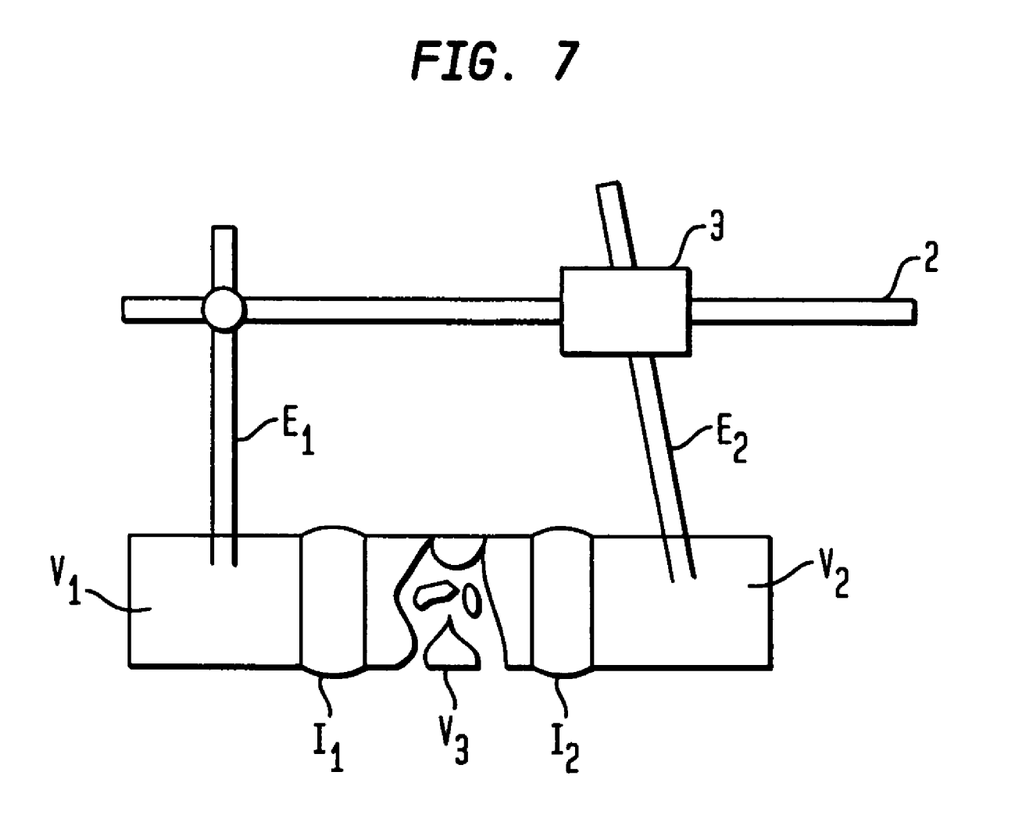
FIG. 7 is a diagrammatic view of the FIG. 1 embodiment in use in an operation.

The operation of the position-adjustment device 1 is described below with reference to FIGS. 5, 6, and 7. A spinal column has a vertebra V3 which presents multiple fractures. This vertebra V3 is associated with two healthy vertebrae V1 and V2 on either side via vertebral disks I1 and I2. As it is known to those of ordinary skill in the art, it is assumed that the elongate member 2 is connected to an element E1 of a surgical instrument that is engaged in the vertebra V1, while the body 3 is connected to a second element E2 of the same surgical instrument that is engaged with the vertebra V2.

The operation of moving the body 3 in the direction of arrow F is described with reference to FIG. 5. For this purpose, the operator applies a force F to plate 14 connected to deformable element 8. This force F enables the deformable element 8 to be moved so as to bring the plate 14 into contact with the face 60 of the half-shell 4 of the body 3, and separate the surfaces 28 of the blades 30 from contact with the surface 56 of the corresponding half-shell. As deformable element 8 moves in the direction of arrow F relative to body 3, by virtue of its circular projections 38 engaging a groove 62 in the elongate member 2, deformable element 8 entrains the elongate member 2 in the direction of arrow F. Thus elongate member 2 is also caused to move, relative to the body 3, in the direction of arrow F. Since the other deformable element 10 has its projections 38 engaged in another groove 62 of the elongate member 2, when the elongate member 2 is entrained in the direction of arrow F, this movement causes deformable element 10 to also move in the direction of arrow F until the surfaces 28 of each of the blades of the second deformable element 10 come into contact with the surface 56 of the half-shell 6. As a result, the second plate 14 connected to the second deformable element 10 is moved away from the face 60 of the second half-shell 6. FIG. 5 depicts this condition.

At this point, while maintaining force F on the first plate 14, the elongate member 2 may be moved in the direction of arrow F', or as otherwise understood through relative movement, body 3 may be moved in the direction of arrow F relative to elongate member 2. Because the projections 38 and the grooves 62 are circular in shape, and because of the new position of deformable element 8 where there is now clearance to allow for the outward radial movement of the various tongues 30 which deform essentially at the groove 36, the projections 38 of the first deformable element 8 escape outwardly from the groove 62 of the elongate member 2 as the elongate member 2 moves in direction F' relative to the body 3, while force F is maintained on the first plate 14.

While moving in the direction of arrow F' relative to body 3, the elongate member 2 entrains the second deformable element 10 to move in direction D. This entrainment is similarly observed from the perspective of body 3 moving in the direction of arrow F relative to elongate member 2. During this entrainment, the surfaces 28 of the second deformable element 10 move away from, and lose contact with, the surface 56 of the half-shell 6, thus moving into a position having a clearance space that will allow for the tongues 30 of the second deformable element 10 to move radially outwardly when necessary. The entrainment of the second deformable element 10 ends when the second plate 14 makes contact with the face 60 of the half-shell 6. At that point, with the continued application of force F on the first plate 14, body 3 may continue to be moved in the direction of arrow F relative to the elongate member 2 over an arbitrary distance, while the projections 38 of the second deformable element 10 move radially out of and into passing grooves 62 of the elongate member 2 which is moving in the direction F' relative to body 3.

Once the body 3 has reached the desired position, the operator ceases to apply the force F that was being exerted on the first plate 14. Deformable element 8 therefore gets entrained by the elongate member 2 moving in direction F' relative to the body 3, and, itself, moves in direction F' relative to body 3 until the faces 28 of each of the tongues 30 of deformable element 8 come into contact with surface 56 of half-shell 4, thereby locking the device in position by holding the projections 38 in the groove 62 under a force D' generated by contact between surface 56 and surfaces 28. FIG. 6 depicts this condition.

Symmetrically, by acting on the second plate 14 in a manner identical to that described above, the operator can move the body 3 in the direction opposite to arrow F.

Similarly, by acting on both plates 14 simultaneously as described above, the operator can cause the body 3 to slide an arbitrary distance in either direction along the elongate member 2 so as to position the body 3 at any desired location.

Naturally, numerous modifications can be made to the invention without thereby going beyond the ambit thereof.

For example, the grooves 62 of the elongate member 2 could be replaced by a knurled surface or by a smooth surface. Under such circumstances, the deformable elements could have a knurled surface instead of projections 38. Locking in a position would then be obtained by means of friction.

The invention claimed is:

1. A position-adjustment device for spinal surgery having controllable movement along a spinal stabilization rod comprising:
   a body having a longitudinal axis and a plane that is perpendicular to said axis, said plane identifying a mid-portion of said body; and
   a first and a second deformable element positioned within said body along said axis and cooperatively arranged with a spinal stabilization rod therein;
   wherein
   said first and second deformable elements are disengageable from said spinal stabilization rod; and
   wherein
   displacement of said body toward said first deformable element so as to decrease a distance between said plane and said first deformable element, identified as a first condition, facilitates unencumbered movement of said device along said spinal stabilization rod in a direction opposite said displacement, identified as a second condition.

2. The position-adjustment device of claim 1, wherein displacement of said first deformable element away from said plane creates a wedging effect upon said spinal stabilization rod by said first deformable element.

3. The position-adjustment device of claim 2, wherein said first deformable element has a bearing surface, and said spinal stabilization rod has a contact surface that interacts with said bearing surface.

4. The position-adjustment device of claim 3, wherein at least one of said bearing surface and said contact surface is smooth.

5. The position-adjustment device of claim 3, wherein said contact surface is knurled.

6. The position-adjustment device of claim 5, wherein said bearing surface has a rounded protrusion for cooperative interengagement with said knurled contact surface.

7. The position-adjustment device of claim 1, wherein said first deformable element has an actuator segment that facilitates user contact thereto.

8. The position-adjustment device of claim 7, wherein said actuator segment is a circular plate.

9. The position-adjustment device of claim 7, wherein said actuator segment is located outside of said body.

10. The position-adjustment device of claim 7, wherein said actuator segment is an abutment that prevents further decrease of said distance between said plane and said first deformable element by externally abutting said body during said placement in said first condition.

11. The position-adjustment device of claim 1, wherein during said first condition, displacement of said body occurs relative to both said first deformable element and said spinal stabilization rod.

12. The position-adjustment device of claim 1, wherein at least one of said first and said second deformable elements is elastic.

13. The position-adjustment device of claim 1, wherein at least one of said first and said second deformable elements is split over all or part of its length.

14. The position-adjustment device of claim 1, further comprising:
a first element coupling said spinal stabilization rod to a first vertebrae; and
a second element coupling said spinal stabilization rod to a second vertebrae.

15. The position-adjustment device of claim 14, wherein said body couples said second element to said spinal stabilization rod.

16. A position-adjustment device comprising:
a body having a first portion and a second portion;
a first elastically deformable element cooperatively arranged with said body at said first portion;
a second elastically deformable element cooperatively arranged with said body at said second portion; and
a spinal stabilization rod slidably arranged through said body and said first and said second elastically deformable elements, said spinal stabilization rod having first and second ends on respective sides as said first and said second portions of said body;
wherein internal wedging of said first elastically deformable element against said first portion of said body restricts movement of said body towards said second end of said spinal stabilization rod because of compressive exertion by said first elastically deformable element upon said spinal stabilization rod; and
wherein displacement of said body toward said first portion of said spinal stabilization rod, and then sustained internal separation of said first elastically deformable element from said first portion of said body, facilitates movement of said body along said spinal stabilization rod toward said second end of said spinal stabilization rod.

17. The position-adjustment device of claim 16, wherein said abutment by said first element against said first portion of said body creates a wedging effect upon said spinal stabilization rod by said first deformable element.

18. The position-adjustment device of claim 17, wherein said first deformable element has a bearing surface, and said spinal stabilization rod has a contact surface that interacts with said bearing surface.

19. The position-adjustment device of claim 18, wherein at least one of said bearing surface and said contact surface is smooth.

20. The position-adjustment device of claim 18, wherein said contact surface is knurled.

21. The position-adjustment device of claim 20, wherein said bearing surface has a rounded protrusion for cooperative interengagement with said knurled contact surface.

22. The position-adjustment device of claim 16, wherein said first deformable element has an actuator segment that facilitates relatively displacing said first deformable element toward said second portion of said body.

23. The position-adjustment device of claim 22, wherein said actuator segment is a circular plate.

24. The position-adjustment device of claim 22, wherein said actuator segment is located outside of said body.

25. The position-adjustment device of claim 22, wherein said actuator segment comes in contact with said body after a length of displacement of said first deformable element toward said second portion of said body, thereby halting further displacement of said first deformable element toward said second portion.

26. The position-adjustment device of claim 16, wherein limited displacement of said first deformable element toward said second portion of said body entrains similar limited displacement of said elongate member relative to said body.

27. The position-adjustment device of claim 16, wherein at least one of said first and said second deformable elements is elastic.

28. The position-adjustment device of claim 16, wherein at least one of said first and said second deformable elements is split over all or part of its length.

29. The position-adjustment device of claim 16, further comprising:
a first element coupling said spinal stabilization rod to a first vertebrae; and
a second element coupling said spinal stabilization rod to a second vertebrae.

30. The position-adjustment device of claim 16, wherein said body couples said second element to said spinal stabilization rod.

* * * * *